(12) United States Patent
Bugnard et al.

(10) Patent No.: US 10,350,033 B2
(45) Date of Patent: Jul. 16, 2019

(54) DENTAL IMPLANT AND KIT INCLUDING SAID DENTAL IMPLANT

(75) Inventors: Guillaume Bugnard, Basel (CH); Ulrich Mundwiler, Basel (CH)

(73) Assignee: STRAUMANN HOLDING AG, Basel (CH)

(*) Notice: Subject to any disclaimer, the term of this patent is extended or adjusted under 35 U.S.C. 154(b) by 0 days.

(21) Appl. No.: 13/391,945

(22) PCT Filed: Aug. 26, 2010

(86) PCT No.: PCT/EP2010/062454
§ 371 (c)(1),
(2), (4) Date: Apr. 18, 2012

(87) PCT Pub. No.: WO2011/023750
PCT Pub. Date: Mar. 3, 2011

(65) Prior Publication Data
US 2012/0196247 A1    Aug. 2, 2012

(30) Foreign Application Priority Data
Aug. 26, 2009 (EP) ..................................... 09168657

(51) Int. Cl.
*A61C 8/00* (2006.01)

(52) U.S. Cl.
CPC ............ *A61C 8/005* (2013.01); *A61C 8/0066* (2013.01); *A61C 8/0089* (2013.01)

(58) Field of Classification Search
CPC ....... A61C 8/005; A61C 8/0066; F16B 23/00; F16B 23/0053
(Continued)

(56) References Cited

U.S. PATENT DOCUMENTS 2,082,748 A * 6/1937 Brown .......................... 411/410
3,584,667 A * 6/1971 Reiland .......................... 81/460
(Continued)

FOREIGN PATENT DOCUMENTS

DE    20 2005 014 637 U1    12/2005
DE    10 2005 005 402 A1    8/2006
(Continued)

OTHER PUBLICATIONS

International Search Report dated Feb. 11, 2011 issued in PCT/EP2010/062454.
(Continued)

*Primary Examiner* — Cris L. Rodriguez
*Assistant Examiner* — Hao D Mai
(74) *Attorney, Agent, or Firm* — Scully, Scott, Murphy & Presser, P.C.

(57) ABSTRACT

A dental implant for insertion in the jaw bone of a patient is provided. The dental implant has an elongated body having a longitudinal axis and a coronal end, an interior bore extending longitudinally from the coronal end, and a plurality of longitudinally extending anti-rotation structures formed at the inner circumference of the interior bore. The anti-rotation structures have a first set of anti-rotation structures constituting a first anti-rotation feature and a second set of anti-rotation structures constituting a second anti-rotation feature which is independent from the first anti-rotation feature. The anti-rotation structures of the first set and the anti-rotation structures of the second set extend in part over a common length along the longitudinal axis.

29 Claims, 11 Drawing Sheets

(58) Field of Classification Search
USPC .................................... 433/173–176, 201.1
See application file for complete search history.

(56) References Cited

U.S. PATENT DOCUMENTS

| | | | | |
|---|---|---|---|---|
| 3,841,371 | A * | 10/1974 | Thurston | 411/276 |
| 4,384,812 | A * | 5/1983 | Miyagawa | 411/410 |
| 4,459,074 | A * | 7/1984 | Capuano | 411/403 |
| 4,960,381 | A * | 10/1990 | Niznick | 433/174 |
| 5,076,788 | A * | 12/1991 | Niznick | 433/173 |
| 5,456,267 | A * | 10/1995 | Stark | 128/898 |
| 5,509,334 | A * | 4/1996 | Shinjo | 81/460 |
| 5,674,036 | A * | 10/1997 | Hsieh | 411/410 |
| 5,810,590 | A | 9/1998 | Fried et al. | |
| 5,904,483 | A * | 5/1999 | Wade | 433/173 |
| 6,131,493 | A * | 10/2000 | Yamamoto et al. | 81/124.7 |
| 6,158,310 | A * | 12/2000 | Goss et al. | 81/121.1 |
| 6,575,057 | B1 * | 6/2003 | Ploeger | 81/53.2 |
| 6,626,067 | B1 * | 9/2003 | Iwinski et al. | 81/121.1 |
| 6,632,057 | B1 * | 10/2003 | Fauchet | 411/403 |
| 6,685,412 | B2 * | 2/2004 | Altarac et al. | 411/403 |
| 7,188,554 | B2 * | 3/2007 | Baynham | 81/436 |
| 7,225,710 | B2 * | 6/2007 | Pacheco, Jr. | 81/460 |
| 7,713,285 | B1 * | 5/2010 | Stone et al. | 606/232 |
| 7,771,459 | B2 * | 8/2010 | von Oepen | 606/301 |
| 8,029,282 | B2 * | 10/2011 | Carter | 433/163 |
| 8,291,795 | B2 * | 10/2012 | Hughes et al. | 81/460 |
| 2003/0059276 | A1 * | 3/2003 | Chen | F16B 23/0092 411/403 |
| 2007/0059666 | A1 | 3/2007 | Zickman et al. | |
| 2007/0154281 | A1 * | 7/2007 | Ward et al. | 411/180 |
| 2008/0261176 | A1 | 10/2008 | Hurson | |
| 2010/0248181 | A1 | 9/2010 | Kremer et al. | |

FOREIGN PATENT DOCUMENTS

| | | |
|---|---|---|
| EP | 1 419 746 A2 | 5/2004 |
| KR | 10-2009-0077982 | 7/2009 |
| WO | WO 2004/080328 A1 | 9/2004 |

OTHER PUBLICATIONS

European Search Report dated Apr. 14, 2010 issued in EP 09168657.6.

Korean Office Action dated May 12, 2016 received from Korean Application No. 2012-7007083, together with an English-language translation.

* cited by examiner

DENTAL IMPLANT AND KIT INCLUDING SAID DENTAL IMPLANT

BACKGROUND

The invention relates to a dental implant, a method for manufacturing the same, a dental implant kit, and a tool for insertion of the dental implant, according to the preambles of the independent claims.

A dental implant is known from EP 1 419 746 A2. The first anti-rotation feature is adapted to engage a driving tool while the second anti-rotation feature is adapted to engage an abutment. After insertion of the dental implant in the jaw bone of a patient, the second anti-rotation feature will be in a pristine condition. The second anti-rotation feature is positioned distal of the first anti-rotation feature in order to provide rotational resistance independent of the first anti-rotation feature. Because the two anti-rotation features are positioned in succession, they require a large longitudinal extension of the inner of the bore, thereby weakening the dental implant, and normally the two anti-rotation features would have to be fabricated one after the other.

U.S. Pat. No. 5,810,590 A discloses another dental implant having two independent anti-rotation features where after insertion of the dental implant in the jaw bone of a patient, the second anti-rotation feature will be in a pristine condition. Two sets of independent anti-rotation structures are formed at a boss inside the implant and extend over a certain common length along the longitudinal axis. However, manufacture of such a boss having anti-rotation structures would be quite complex.

SUMMARY

It is the object of the invention as claimed to overcome the above problems and to provide a very compact dental implant having independent anti-rotation features which can be manufactured a lot easier.

According to the invention, the anti-rotation structures of a first set and the anti-rotation structures of a second set are formed at least over a common length along the longitudinal axis.

Therefore, the length of the bore which is necessary to shape the anti-rotation structures therein can be short, preferably as short as the bore of a well-known conventional dental implant having a bore with common anti-rotation structures therein used both for insertion of the implant into the bone and for engagement of an abutment. Thus the dental implant of the invention is quite compact and stable, in particular much more compact and stable than the dental implants according to the state of the art as indicated initially.

Further, the first set of equally profiled anti-rotation structures can be formed supplementary to a second set of equally profiled anti-rotation structures which are shaped like the common anti-rotation structures of said well-known conventional dental implants. However, according to the invention, the second set of anti-rotation structures will be used exclusively to attach abutments, and accordingly there is no need to modify the well-known conventional abutments.

Although the first and second anti-rotation features extend over a common length, it is preferable that these do not extend only over this common length, in other words that the first and second features are not identical in both position and length. Instead, preferably the anti-rotation structures of the first set and the anti-rotation structures of the second set are formed only in part over a common length.

Therefore, according to a particularly preferred aspect, the present invention provides a dental implant for insertion in the jaw bone of a patient, comprising an elongated body having a longitudinal axis and a coronal end, an interior bore extending longitudinally from the coronal end, and a plurality of longitudinally extending anti-rotation structures formed at the inner circumference of the interior bore, with a first set of anti-rotation structures constituting a first anti-rotation feature and a second set of anti-rotation structures constituting a second anti-rotation feature which is independent from the first anti-rotation feature, characterized in that the anti-rotation structures of the first set and the anti-rotation structures of the second set extend in part over a common length along the longitudinal axis.

According to this embodiment the first set of anti-rotation structures extend over a first length of the longitudinal bore and the second set of anti-rotation structures extend over a second length of the longitudinal bore, wherein the first and second lengths are not identical in both position and value. Therefore in this embodiment the lengths do not have the same start and end locations within the bore. While it is possible for the first and second lengths to have same value, these must then be staggered within the bore. Equally it is possible for both lengths to have the same start or end point, but not both, i.e. when both sets of structures begin or end in the same location their lengths must be different. In this embodiment, although the first and second anti-rotation features overlap over a common length, they are not in complete alignment. This enables each anti rotation feature to be positioned and dimensioned in a manner particularly suited for its intended function whilst still minimising the length of the longitudinal bore.

For example, when the first set of anti-rotation structures are intended for operative engagement with an insertion tool, such that torque can be transmitted from the tool to the implant via the first anti-rotation feature, it is preferable for the first set of anti-rotation structures to extend over a greater length of the longitudinal bore than the second set of anti-rotation structures. This gives a greater surface area for torque transmission. In addition, or alternatively, the first set of anti-rotation structures may begin closer to the coronal end of the implant than the second set. By locating the first set of anti-rotation structures closer to the top of the implant it is easier for these to be engaged by an insertion tool.

Preferably the second set of anti-rotation structures are totally encompassed by the first set of anti-rotation structures. In this way the second set of anti-rotation structures do not affect the overall length of the bore as these are totally contained within the first set. Preferably the anti-rotation structures of the second set have a length of between ⅓ to ½ of the first set.

In order to create a secure connection between the implant and abutment it is known to provide a tapered section at the coronal end of the longitudinal bore. The connection portion of the abutment has a matching taper, which enables a good, sealed connection between the two components.

Preferably therefore, the bore comprises, at its coronal end, a frustoconical surface tapering inwardly, wherein the common length of the first and second anti-rotation structures is located apical of this surface. Providing a tapered surface at the coronal end of the implant which is free from anti-rotation structures ensures a sealed engagement between the implant and abutment and thus prevents bacteria from entering the bore. This is particularly important in the present case as the abutment will not engage all of the anti-rotation structures. As gaps will thus exist between the abutment and, for example, the first set of anti-rotation structures, it is beneficial for a complete seal to be formed coronal of these structures.

This is considered to be inventive in its own right and therefore, viewed from another aspect, the present invention provides a dental implant for insertion in the jaw bone of a patient, comprising an elongated body having a longitudinal axis and a coronal end, an interior bore extending longitudinally from the coronal end, comprising an inwardly tapered frustoconical surface extending from the coronal end, and, apically adjacent to the frustoconical surface a cylindrical portion, wherein the bore further comprises a first set of equally profiled longitudinally extending anti-rotation structures constituting a first anti-rotation feature and a second set of equally profiled longitudinally extending anti-rotation structures constituting a second anti-rotation feature, the anti-rotation structures of the first and second set extending at least over a common length along the longitudinal axis apical of the frustoconical surface.

In the context of the present invention "frustoconical surface" simply means a truncated conical surface, i.e. the surface tapers from a first radius to a second, smaller radius.

In a preferred embodiment the first set of anti-rotation structures begins in said frustoconical surface and the second set begin apically of said frustoconical surface. In this embodiment, the first set of anti-rotation structures are used in combination with an insertion tool to transmit torque to the implant and the second set are used in combination with an abutment to prevent relative rotation between the abutment and the implant. By positioning the first set of anti-rotation structures partially within the frustoconical surface of the bore these can be closer to the coronal end of the implant and greater in length. Locating the second anti-rotation feature apical of the frustoconical surface eases construction of the abutment and also allows conventional abutments to be used in the implant of the present invention.

The first set of anti-rotation structures start within the bore but do not extend to the coronal end of the implant. In this embodiment therefore the upper, coronal most section of conical surface remains smooth walled and thus ensures a sealed engagement between the implant and abutment. For example the first set of anti-rotation structures may start at least 0.3 mm, e.g. 0.5 mm, into the bore.

Each anti-rotation feature must comprise at least one surface having a radial dimension. An object in contact with this surface is thus prevented from rotating about the longitudinal axis and torque can be transmitted between the object and the implant. Each anti-rotation structure thus comprises at least one anti-rotation surface and more preferably at least two, such that the structure can provide rotational resistance in both directions.

The anti-rotation structures of each set are preferably located at regularly spaced angular intervals. This helps to evenly distribute force about the implant axis. To the same end the anti-rotation structures of the first set are preferably equally profiled and the anti-rotation structures of the second set are preferably equally profiled, but different to the first set. This difference in shape prevents the insertion tool or abutment from engaging the wrong anti-rotation feature. It is also possible for each anti-rotation feature to comprise a plurality of sets of differently profiled structures. In order to distribute forces evenly about the implant axis these sets should be arranged such that the anti-rotation feature is symmetrical about at least one line of symmetry lying perpendicular to the longitudinal axis. For example the anti-rotation feature may comprise two differently profiled sets of structures arranged alternately about the longitudinal axis. For ease of construction however all of the anti-rotation structures of each anti-rotation feature are preferably equally profiled.

The first and second anti-rotation features preferably comprise anti-rotation surfaces which are situated at discrete angular positions relative to one another. In this way an insertion tool can be shaped for contact with the anti-rotation surfaces of the first feature without contacting the anti-rotation surfaces of the second feature. Thus the second anti-rotation feature can be kept pristine for contact with a dental abutment.

In order to create anti-rotation structures having radially dimensioned surfaces, it is known in existing implants for the longitudinal bore to comprise grooves, these grooves forming the anti-rotation structures. However, by removing material from the implant the strength of the implant is reduced. Therefore, in a preferred embodiment the anti-rotation structures of at least one of the anti-rotation features are formed by projections (protrusions) on the interior bore. In such embodiments, the common length of the bore over which the first and second anti-rotation features overlap can be circular cylindrical in shape and have a radius r. The at least one set of anti-rotation structures thus comprise projections which extend inwardly of r. In other embodiments the common length may have another elliptical base shape in the plane perpendicular to the longitudinal axis, the projections protruding inwardly of this base shape. The provision of projections strengthens the implant as less material is removed in the formation of the interior bore. As mentioned above, the anti-rotation structures of each set are preferably located at regularly spaced angular intervals, thus the projections are interposed between segments of the bore having an elliptical surface, e.g. having radius r in the case of a circular cylindrical bore.

This is considered inventive in its own right and therefore, viewed from a further aspect, the present invention comprises a dental implant for insertion in the jaw bone of a patient, comprising an elongated body having a longitudinal axis and a coronal end, an interior bore extending longitudinally from the coronal end, with a first set of longitudinally extending anti-rotation structures constituting a first anti-rotation feature and a second set of longitudinally extending anti-rotation structures constituting a second anti-rotation feature, the anti-rotation structures of the first set and the anti-rotation structures of the second set extending at least in part over a common length of the bore, wherein at least one set of anti-rotation structures are formed by projections on the interior bore.

It is possible for both anti-rotation features to be formed by separate, differently profiled sets of projections. However preferably the other set of anti-rotation structures are formed by indentations, i.e. grooves. In a particularly preferred embodiment at least some of the anti-rotation structures of the other, e.g. first, anti-rotation feature are formed by grooves formed within the projections. In one preferred embodiment all of the anti-rotation structures of the other feature are formed within the projections. In this way the first and second anti-rotation features are fitted into, or superimposed onto each other (interleaved). When the indentations are fully contained within the projections both sets of anti-rotation surfaces extend inwards of r, but not beyond r. This eases construction of the anti-rotation means.

In alternative embodiments the grooves may extend into the main body of the implant, i.e. the grooves can extend beyond r. The grooves can either be formed in the projections or in the elliptical wall of the interior bore, or both.

Creating the first set of anti-rotation structures as grooves which extend into the implant body increases the length of the lever arm of the corresponding insertion tool and hence increases the torque transferred to the implant.

In a preferred embodiment the first and second sets of anti-rotation structures extend over a common length of the bore having a radius r, wherein the first set of anti-rotation structures comprise anti-rotation surfaces located radially beyond r and the second set of anti-rotation structures comprise anti-rotation surfaces located inwards of r. In this way the anti-rotation surfaces of the first and second anti-rotation features are radially as well as angularly spaced.

In order to insert the dental implant in the bone a special tool is required for engagement into the first set of anti-rotation structures while maintaining the second set of anti-rotation structures in a pristine condition.

A very appropriate tool for cooperation with the dental implant of the invention has a tip which is profiled to occupy almost the whole cross section of an anti-rotation structure-part of the interior bore while being in form fit with the first set of anti-rotation structures. The tool tip may be profiled so that it does not contact the second set of anti-rotation structures when inserted, or it may be profiled so that a slight contact with the second set of anti-rotation structures is possible, which contact does not damage the second set of anti-rotation structures.

A very advantageous tool for insertion of a dental implant into the bone of a patient comprises a tip with a constant cross section in the direction of a longitudinal axis of the tool, wherein the cross section of the tip consists of a polygon, in particular a square, having plane sides and flattened corners extending along the longitudinal axis and of a plurality of longitudinally extending projections which have a rounded or curved convex profile and which are arranged equidistantly at the outer circumference of the tip, wherein each flattened corner of the polygon bears one of the projections and/or each plane side of the polygon bears one of the projections.

Viewed from a further aspect the present invention provides a kit comprising an implant as herein described and an insertion tool comprising at its distal end a tip shaped to engage the first set of anti-rotation structures such that torque can be transmitted from the tool to the implant via the first anti-rotation feature, the tip being further shaped to not engage the second set of anti-rotation structures in a torque transmitting manner.

Preferably the kit further comprises an abutment for connection to the implant, the abutment comprising a connection portion for insertion into the longitudinal bore of the implant, wherein the connection portion comprises an anti-rotation feature shaped to engage the second set of anti-rotation structures without engaging the first set of anti-rotation structures.

The dental implant according to the invention would be easy to manufacture. In particular the anti-rotation structures at the inner circumference of the interior bore can be formed by a shaper, for example by means of one or two shaping tools without re-clamping or rearranging the workpiece and the tool(s), respectively.

DESCRIPTION OF DRAWINGS

The above and other features and advantages of the invention will become apparent and more readily appreciated from the following description of example embodiments in conjunction with the accompanying drawings, in which.

DETAILED DESCRIPTION OF THE EMBODIMENTS

Figure 1:
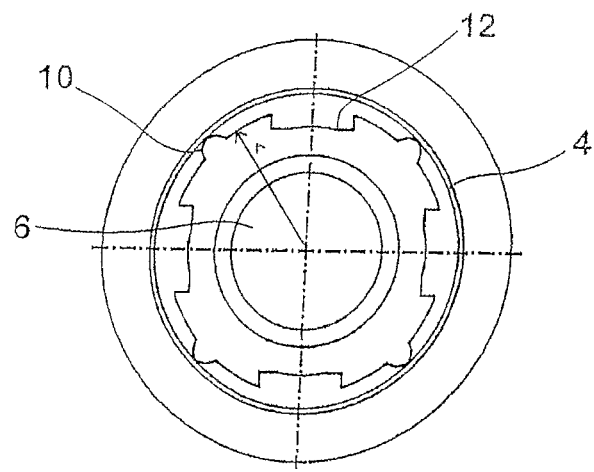
FIG. 1 shows a top view from the coronal end of a dental implant according to a first embodiment of the invention.
Figure 2:
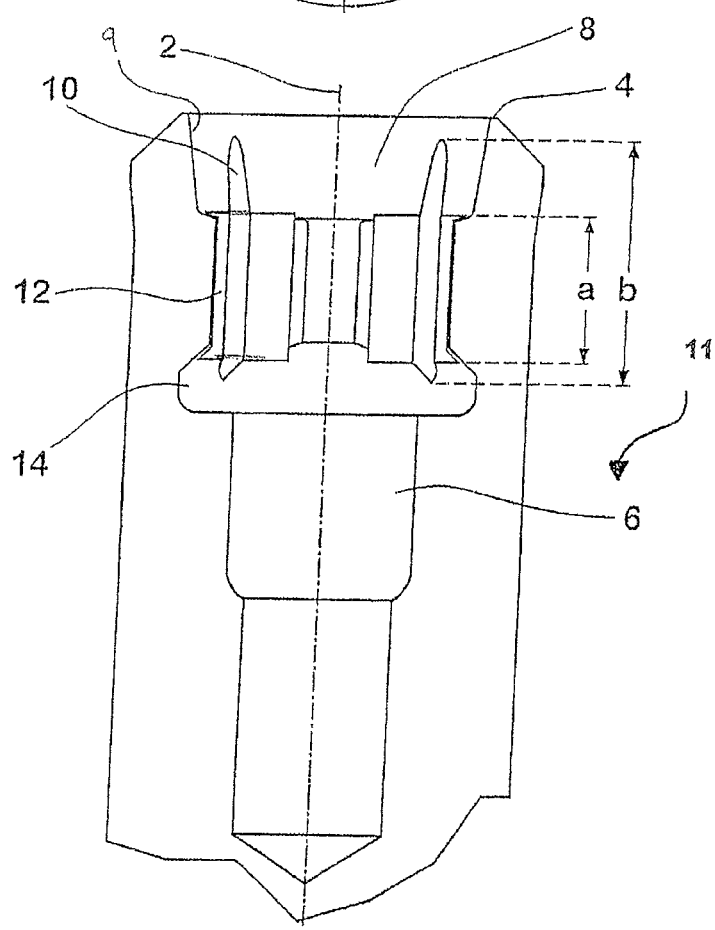
FIG. 2 shows a partial longitudinal section of the dental implant according to the first embodiment.

As shown in FIGS. 1 and 2, a dental implant for insertion in the jaw bone of a patient comprises an axially symmetric elongated body having a longitudinal axis 2 and a coronal end 4 generally transverse to the longitudinal axis 2. In the longitudinal section, the dental implant is not shown along its whole length, so that an apical end thereof having threads for insertion in the jaw bone is not seen in the drawings.

From the coronal end 4 a stepped interior bore 6, which is a blind hole having internal threads in its lower part, extends along the longitudinal axis 2 into the dental implant. At an inner circumference of a proximal part 8 of the bore 6 there are formed a plurality of anti-rotation structures. The bore 6, in the region of at least the common length of the anti-rotation structures, has a base circular cylindrical shape, with radius r, on which the anti-rotation structures have been formed. In other embodiments this length may have an alternative elliptical base (in which $e \neq 0$) and could be conical rather than cylindrical.

A first set of equally profiled anti-rotation structures comprises four longitudinally extending grooves or indentations 10 in the inner circumference of the bore 6. All indentations 10 have the same semi-circular profile or contour. The four indentations 10 are distributed equidistantly at the inner circumference of the bore 6. The four indentations 10 constitute a first anti-rotation feature which is engaged by an appropriately shaped tool when inserting the implant in a jaw bone.

These indentations 10 provide anti-rotation surfaces having a radial dimension and which extend radially beyond the radius r of the common length a of the bore.

A second set of equally profiled anti-rotation structures comprises four longitudinally extending projections 12 on the inner circumference of the bore 6. All the projections 12 have the same flat, approximately rectangular profile or contour. The four projections 12 are distributed equidistantly at the inner circumference of the bore 6 and alternate with the indentations 10 in that the projections 12 are displaced by 45 degree with respect to the indentations 10. The four projections 12 constitute a second anti-rotation feature which is engaged by an appropriately shaped abutment carrying a dental crown or an abutment forming a secondary part, when the abutment is mounted to the implant.

The lateral faces of the projections 12 provide anti-rotation surfaces. These extend radially inwards of the radius r. In addition or alternatively the end face of the projections 12 can also act as an anti-rotation surface.

As seen in the longitudinal section of FIG. 2, the indentations 10 extend over a length b along the longitudinal axis 2, while the projections 12 extend over a length a along the longitudinal axis 2, wherein the length a is encompassed by and approximately ½ or ⅔ of the length b. Thus, the indentations 10 and the projections 12 extend over a common length a along the longitudinal axis without being identical. In other embodiments, not shown here, it is possible for the indentations 10 and projections 12 to be staggered such that the common length c is formed by the overlap of lengths a and b.

The indentations 10 and projections 12 create a complex geometrical cross section over the common length a of the bore 6. However, the base circular cylindrical shape is still clearly identifiable and segments of the bore 6 conforming to this base shape are interposed between the anti-rotation structures.

Because the indentations 10 have a profile transverse to the longitudinal axis 2 which is completely different from the profile of the projections 12, the present invention reliably prevents the tool for insertion 111 of the dental implant in the bone from engaging or damaging the projections 12 in any way or that the abutment engages or damages the indentations 10 in any way when the tool or the abutment is inserted into the proximal part 8 of the bore 6. Thus, while one type of the anti-rotation structures 10 or 12 is being used, the other one is maintained reliably in a pristine condition.

Below the anti-rotation structures in the direction of the longitudinal axis 2, the proximal part 8 of the bore 6 has an expanded area in the form of an undercut 14. The undercut 14 facilitates the machining of the indentations 10 and projections 12 by a shaper, for example by means of one or two shaping tools reciprocating along the longitudinal axis 2. Because the indentations 10 and projections 12 are situated substantially in the same plane vertical to the longitudinal axis 2, they can be shaped without re-clamping or rearranging the implant workpiece and the shaping tool (s), respectively.

Above the anti-rotation structures in the direction of the longitudinal axis 2, the coronal part of the bore 6 comprises an inwardy tapered frustoconical portion 9. The indentations 10 of the first anti-rotation feature begin within this tapered portion 9 but at a location removed from the coronal end 4 of the implant. This allows a tight seal to be formed between the implant and abutment while also enabling the first set of anti-rotation structures to be placed higher in the bore than the second set.

Figure 3:
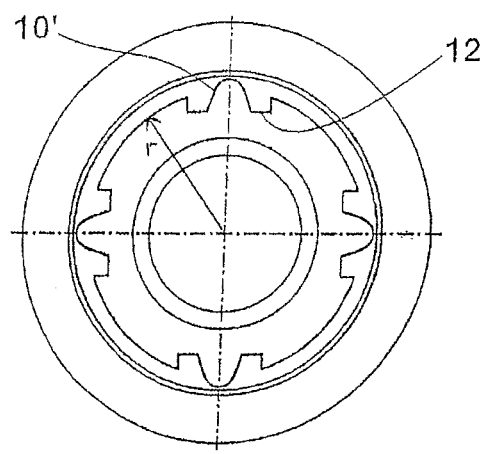
FIG. 3 shows a top view from the coronal end of a dental implant according to a second embodiment of the invention.
Figure 4:
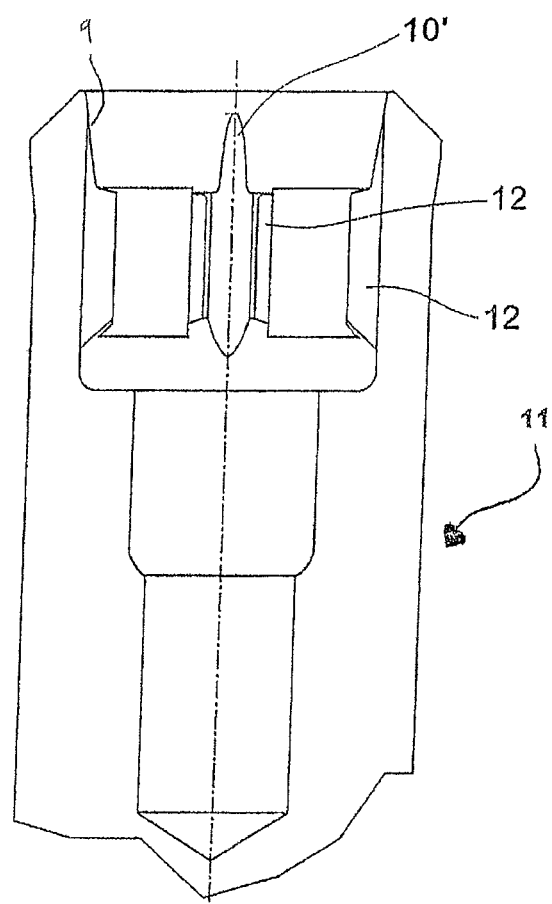
FIG. 4 shows a partial longitudinal section of a dental implant according to the second embodiment.
Figure 8:
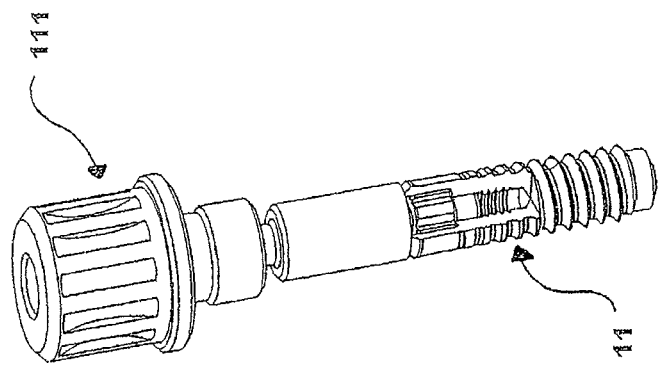
Figure 7:
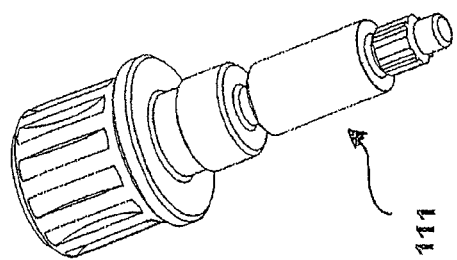
Figure 6:
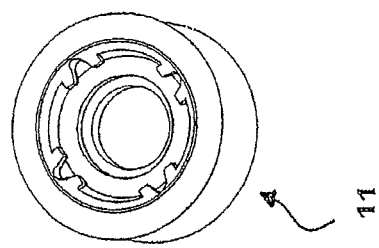
FIGS. 5 and 6 show perspective views of the dental implant of FIGS. 3 and 4 and FIGS. 7 and 8 show perspective views of a tool for insertion of the dental implant in the bone.
Figure 5:
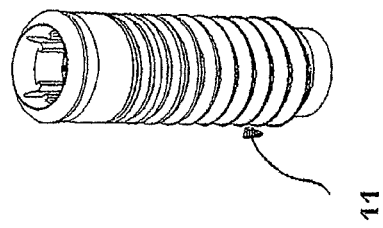
Figure 12:
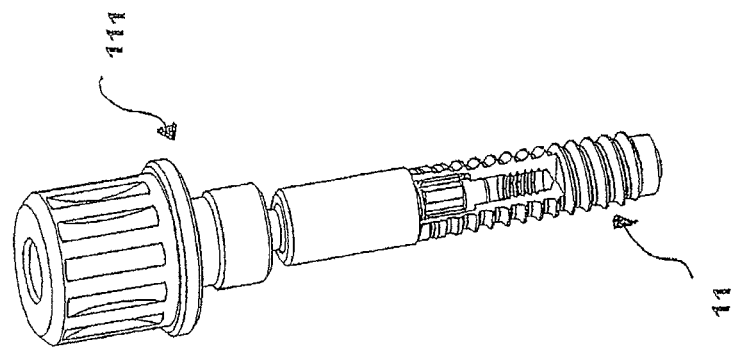
Figure 11:
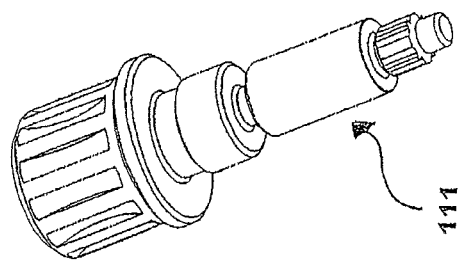
Figure 10:
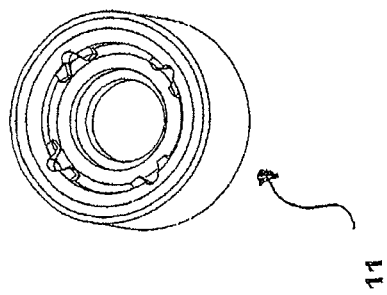
FIGS. 9 and 10 show perspective views of a modification of the dental implant of FIGS. 3 and 4 and FIGS. 11 and 12 show perspective views of a tool for insertion of the dental implant in the bone.
Figure 9:
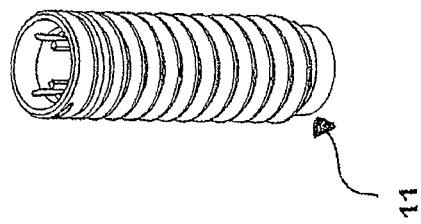

FIGS. 3 and 4 show a dental implant similar to the dental implant of FIGS. 1 and 2 with the only difference that the four indentations 10' and four projections 12 are not arranged alternating with each other or displaced by 45 degrees at the inner circumference of the bore. Instead, by locating the indentations 10', which are profiled in correspondence to the indentations 10 in FIGS. 1 and 2, and the projections 12 at the same angular positions, they are fitted into each other or interleaved with each other in the sense that each indentation 10 is shaped in the middle of one of the broader projections 12.

Despite the interleaved nature of the first and second sets however, the anti-rotation surfaces are kept angularly distinct from one another. In this way an object shaped to contact the anti-rotation surfaces of the first anti-rotation feature need not also contact the anti-rotation surfaces of the second feature.

In this embodiment the anti-rotation surfaces of the indentations 10' extend both radially beyond and inwards of radius r. Forming the indentations 10' within the protrusions 12 increases the surface area of the anti-rotation surfaces of the first anti-rotation feature without deepening the depth of the indentations 10' and hence weakening the implant. Once again the circular base shape is observable in the intervening segments having radius r.

FIGS. 5-8 show from left to right a perspective view of dental implant of FIGS. 3 and 4, an enlarged perspective view dental implant of FIGS. 3 and 4, a perspective view of a tool for insertion 111 of the dental implant of FIGS. 3 and 4 in the bone, and a perspective view of the dental implant and the tool as interlocked with each other. Please note that the enlarged perspective view is taken from a position almost vertical above the dental implant so that the longitudinally extending structures therein appear extremely shortened. The same holds for the corresponding perspective views of FIGS. 9-12, 15-18, 19-22, 27-30 and 31-34.

FIGS. 9-12 show corresponding perspective views of a modification of the dental implant of FIGS. 3 and 4. While the dental implant of FIGS. 3 and 4 and FIGS. 5-8 is a tissue level implant, the dental implant of FIGS. 9-12 is a bone level implant. The internal structure of the longitudinal bore 6 however remains unchanged.

Figure 13:
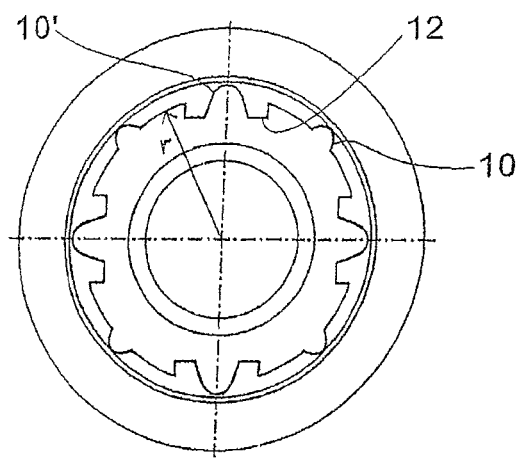
FIG. 13 shows a top view from the coronal end of a dental implant according to a third embodiment of the invention.
Figure 14:
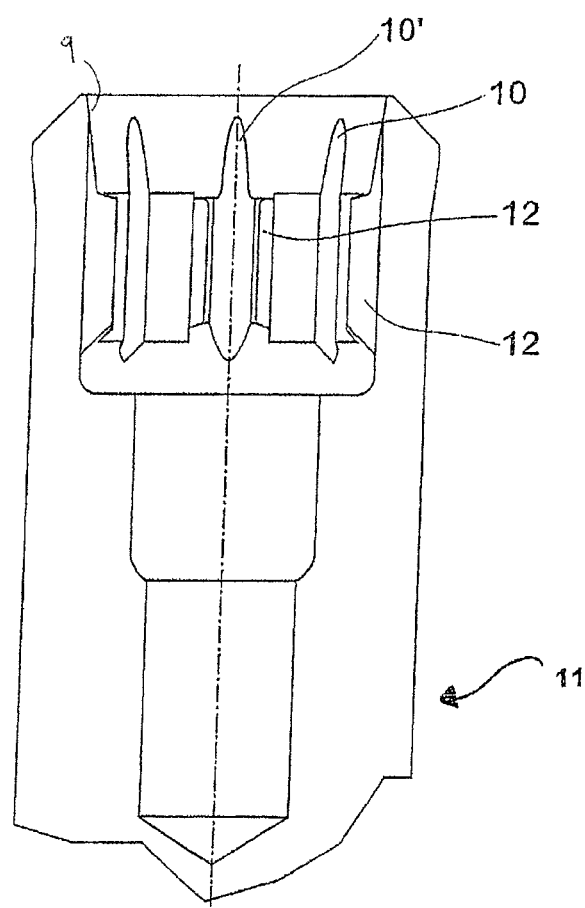
FIG. 14 shows a partial longitudinal section of a dental implant according to the third embodiment.
Figure 18:
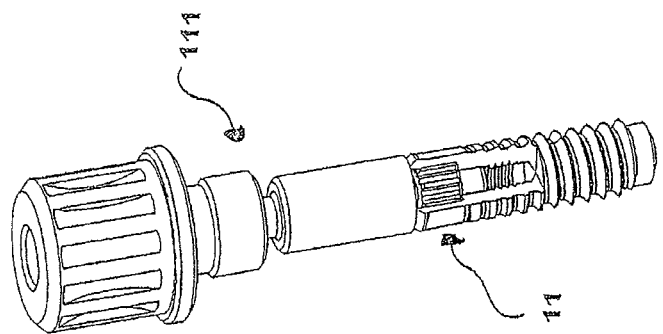
Figure 17:
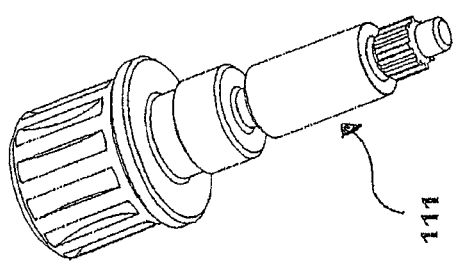
Figure 16:
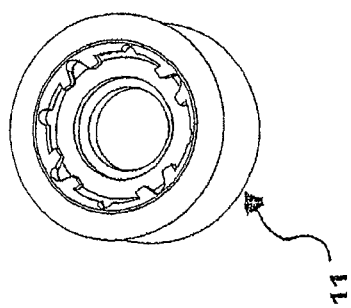
FIGS. 15 and 16 show perspective views of the dental implant of FIGS. 13 and 14 and FIGS. 17 and 18 show perspective views of a tool for insertion of the dental implant in the bone.
Figure 15:
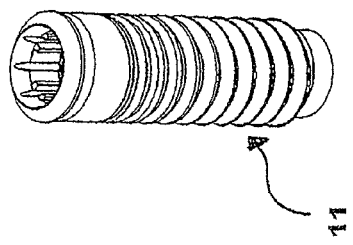
Figure 22:
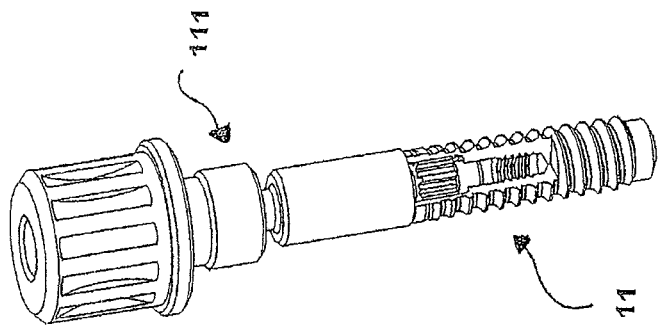
Figure 21:
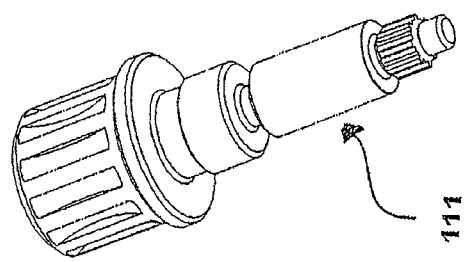
Figure 20:
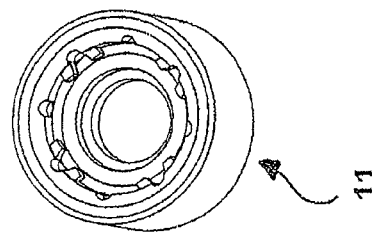
FIGS. 19 and 20 show perspective views of a modification of the dental implant of FIGS. 13 and 14 and FIGS. 21 and 22 show perspective views of a tool for insertion of the dental implant in the bone.
Figure 19:
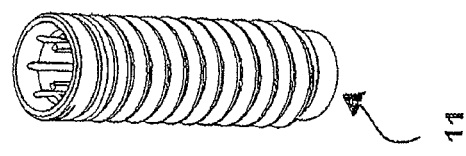

FIGS. 13 and 14 show a dental implant similar to the dental implant of FIGS. 3 and 4 with the only difference that four additional indentations 10 are provided which are profiled and arranged in the same way as the indentations 10 in FIGS. 1 and 2. The first anti-rotation feature is constituted by the eight equidistantly arranged indentations 10 and 10'. As can be seen from FIGS. 13 and 14, each of the indentations 10, 10' has the same semi-circular profile or contour, however indentations 10' are larger as these are located within protrusions 12. It would also be possible for indentations 10' to have a different profile to indentations 10 as long as the profile shape fitted within projection 12. The symmetrical nature of the arrangement of indentations 10, 10' would allow for good, even torque transmission about the axis of the implant even when indentations 10, 10' have different profiles.

The implants of FIGS. 3, 4, 13 and 14 have the same inwardly tapered portion 9 described in relation to FIGS. 1 and 2, with the indentations 10, 10' of the first anti-rotation feature beginning within this inwardly tapered portion 9.

FIGS. 15-18 show from left to right a perspective view of the tissue level dental implant of FIGS. 13 and 14, an enlarged perspective view of the dental implant of FIGS. 13 and 14, a perspective view of a tool for insertion 111 of the dental implant of FIGS. 13 and 14 in the bone and a perspective view of the dental implant and the tool as interlocked with each other. FIGS. 19-22 show corresponding perspective views of a bone level modification of the dental implant of FIGS. 13-18.

Figure 23:
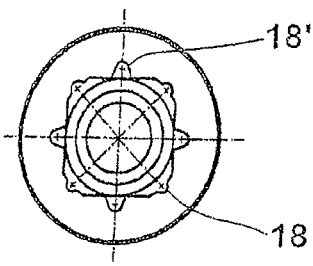
FIG. 23 shows a top view of a tool for insertion of the dental implant in the bone.
Figure 24:
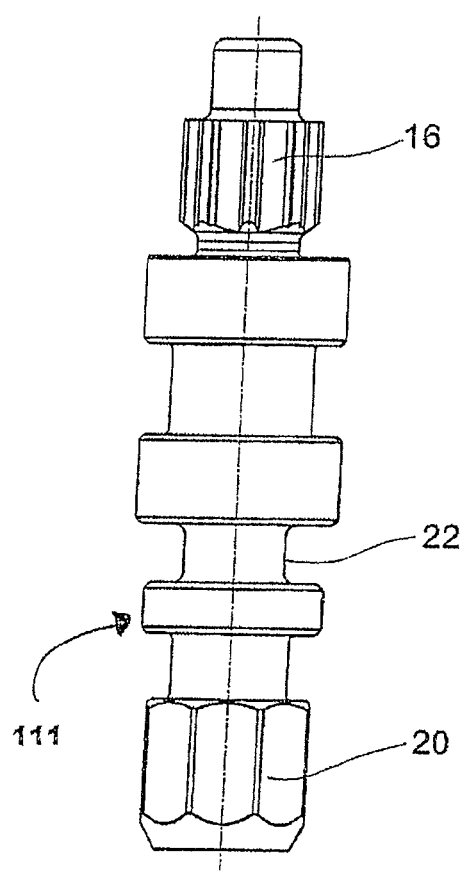
FIG. 24 shows a lateral view of a tool for insertion of the dental implant in the bone.

FIGS. 23 and 24 show in more detail the elongate bit tool which is used for insertion of a dental implant as shown in FIGS. 13 and 14 into the jaw bone of a patient. Although FIGS. 23 and 24 are scaled down against FIGS. 13 and 14, it is seen that the cross section of an implant side tip 16 of the tool occupies almost the whole cross section of the area of the interior bore which bears the anti-rotation structures 10, 10' and 12 in FIGS. 13 and 14.

Eight longitudinally extending projections 18 and 18' are arranged equidistantly at the outer circumference of the implant side tip 16 of the tool. When the tool is inserted axially into the proximal part 8 of the bore 6 (cf. FIGS. 1 and 2) of the dental implant, the eight projections 18 and 18' engage with the eight indentations 10 and 10' and are in form fit therewith. At the same time, the tool nowhere contacts the projections 12 of the dental implant.

In particular, the tool tip 16 has a constant cross section in the direction of a longitudinal axis of the tool, and the cross section of the tip 16 consists of a square having plane sides and flattened corners extending along the longitudinal axis and of eight longitudinally extending projections 18 and 18' which have a rounded or curved convex profile. Each flattened corner of the square bears one of the four projections 18, and each plane side of the square bears one of the projections 18'.

In order to get a tool tip suited for the dental implant of FIGS. 1 and 2, the four projections 18' would be omitted, and in order to get of a tool tip suited for the dental implant of FIGS. 3 and 4, the four projections 18 would be omitted.

At a driving side end 20 of the tool, there is formed a standard hexagon 20 for engagement by a standard driving tool which is driven manually in order to screw the dental implant into the bone.

Between the tool tip 16 and the driving side end 20 of the tool, the tool has a necking 22 or reduction in its cross section which forms a breaking point in order to prevent overturning when the dental implant is screwed into the bone.

Figure 25:
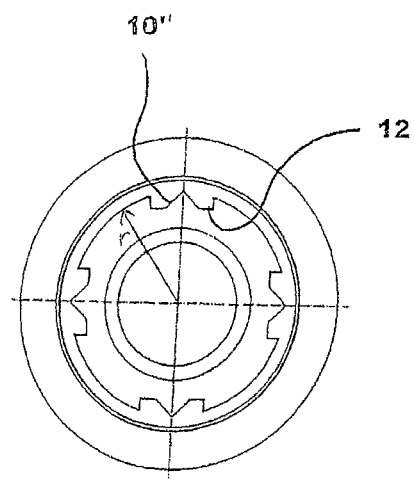
FIG. 25 shows a top view from the coronal end of a dental implant according to a fourth embodiment of the invention.
Figure 26:
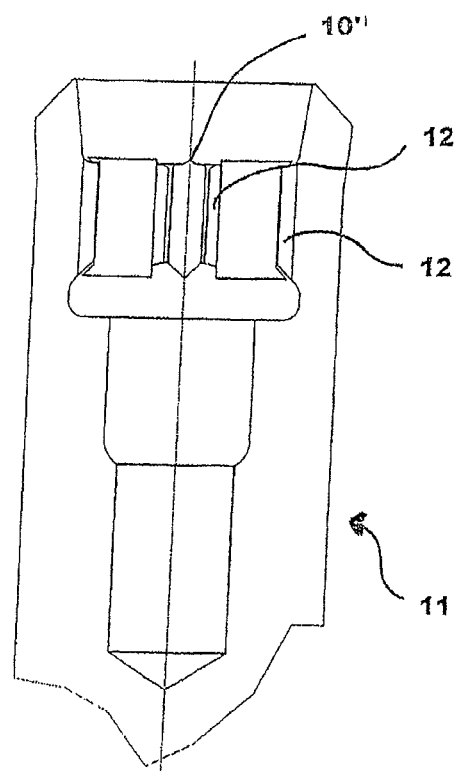
FIG. 26 shows a partial longitudinal section of a dental implant according to the fourth embodiment.
Figure 30:
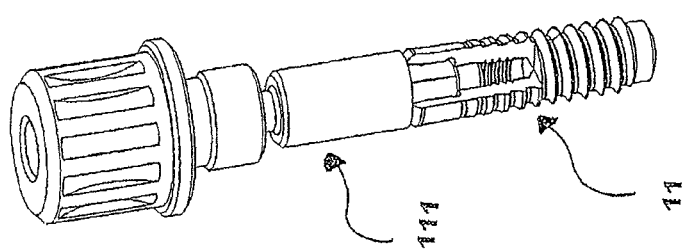
Figure 29:
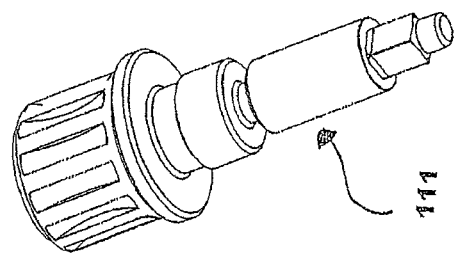
Figure 28:
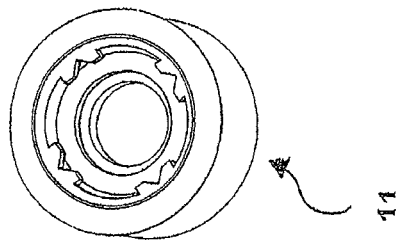
FIGS. 27 and 28 show perspective views of the dental implant of FIGS. 25 and 26 and FIGS. 29 and 30 show perspective views of a tool for insertion of the dental implant in the bone.
Figure 27:
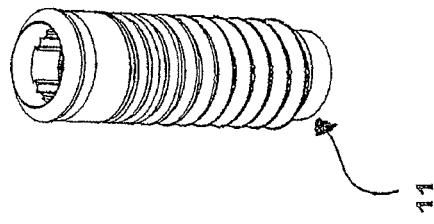
Figure 34:
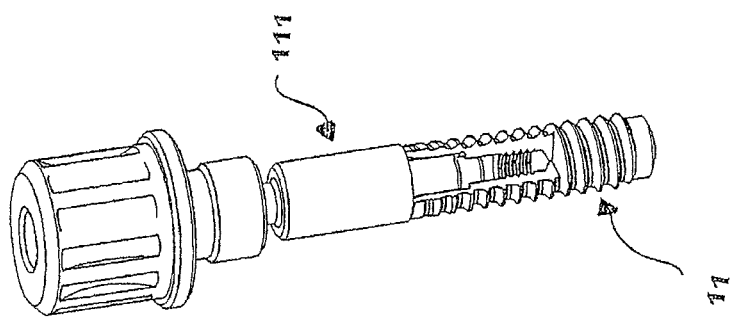
Figure 33:
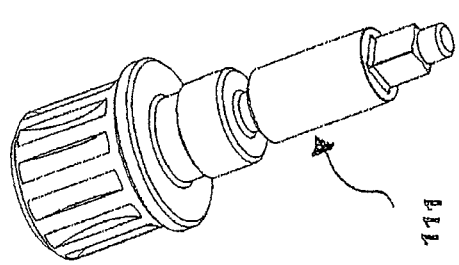
Figure 32:
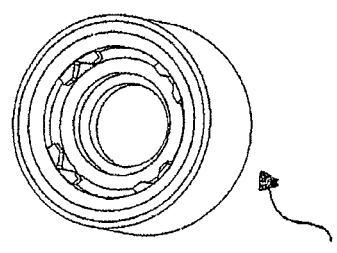
FIGS. 31 and 32 show perspective views of a modification of the dental implant of FIGS. 25 and 26 and FIGS. 33 and 34 show perspective views of a tool for insertion of the dental implant in the bone.
Figure 31:
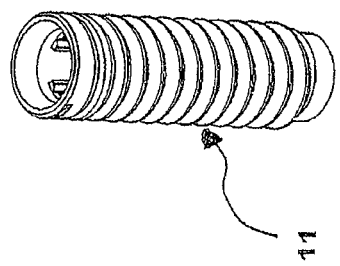

FIGS. 25 and 26 show a top view from the coronal end and a partial longitudinal section of a dental implant according to a fourth embodiment of the invention. This embodiment is similar to the embodiment of FIGS. 3 and 4 in that indentations 10" are located within the projections 12. However, in this embodiment indentations 10" have not a semi-circular but a triangular profile or contour. In addition these are completely contained within the projections, i.e., the indentations do not extend beyond radius r. As such the indentations 10" are formed only in the projections 12 and not in the implant body. This eases manufacture of the two anti-rotation features and strengthens the implant.

In this embodiment the projections 12 and indentations 10" are completely aligned in the longitudinal direction. It is not possible for the indentations 10" to have a greater longitudinal length than the projections 12 as these do not extend radially beyond r.

FIGS. 27-30 show from left to right a perspective view of the tissue level dental implant of FIGS. 25 and 26, an enlarged perspective view of the dental implant of FIGS. 25 and 26, a perspective view of a tool for insertion 111 of the dental implant of FIGS. 25 and 26 in the bone and a perspective view of the dental implant and the tool as interlocked with each other. FIGS. 31-34 show corresponding perspective views of a bone level modification of the dental implant of FIGS. 25-30.

It is recognized from FIGS. 25-34 that in this embodiment the implant side tip of the tool may have a more simple profile or contour, namely a square profile or contour.

The above described embodiments are for illustrative purposes only and the skilled man will realize that many alternative arrangements are possible which fall within the scope of the claims. In particular, the specific shape and positioning of the anti-rotation structures can be altered.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

According to one aspect the present invention comprises a dental implant for insertion in the jaw bone of a patient, comprising an elongated body having a longitudinal axis and a coronal end generally transverse to the longitudinal axis, an interior bore extending longitudinally from the coronal end, and a plurality of longitudinally extending anti-rotation structures formed at the inner circumference of the interior bore, with a first set of equally profiled anti-rotation structures constituting a first anti-rotation feature and a second set of equally profiled anti-rotation structures constituting a second anti-rotation feature which is independent from the first anti-rotation feature, characterized in that the anti-rotation structures of the first set and the anti-rotation structures of the second set extend at least over a common length along the longitudinal axis.

Preferably the common length along the longitudinal axis amounts to at least the half of the length of longer ones of the anti-rotation structures.

Preferably the anti-rotation structures of the first set have another profile transverse to the longitudinal axis than the anti-rotation structures of the second set.

Preferably the anti-rotation structures of one of the two sets have a rounded or curved profile and the anti-rotation structures of the other set have an angled profile.

Preferably the anti-rotation structures of one of the two sets are broader than the anti-rotation structures of the other set.

Preferably the anti-rotation structures of one of the two sets are projections on the interior bore and the anti-rotation structures of the other set are indentations in the interior bore.

Preferably the anti-rotation structures of the first set and of the second set are arranged equidistantly at the inner circumference of the interior bore.

Preferably the anti-rotation structures of the first set and of the second set are arranged alternating at the inner circumference of the interior bore.

Preferably at least some of the anti-rotation structures of the first set and of the second set are interleaved with each other.

Preferably the anti-rotation structures are formed at the inner circumference of the interior bore by a shaper and/or are hard machined.

According to another aspect the present invention comprises a dental implant kit comprising at least one dental implant as described herein and a tool for insertion of the dental implant in the bone by engagement into the first set of anti-rotation structures, the tool having a tip which is profiled to occupy almost the whole cross section of an anti-rotation structure-part of the interior bore while being in form fit with the first set of anti-rotation structures.

According to another aspect the present invention comprises a tool for insertion of a dental implant as described herein, comprising a tool tip with a constant cross section in the direction of a longitudinal axis of the tool, wherein the cross section of the tip consists of a polygon having plane sides and flattened corners extending along the longitudinal axis and of a plurality of longitudinally extending projections which have a rounded or curved convex profile and which are arranged equidistantly at the outer circumference of the tip, wherein each flattened corner of the polygon bears one of the projections and/or each plane side of the polygon bears one of the projections.

Preferably the polygon is a square.

Preferably the tool has a necking which represents a breaking point.

The invention claimed is:

1. A dental implant for insertion in the jaw bone of a patient, comprising:
    an elongated body having a longitudinal axis and a coronal end,
    an interior blind bore extending longitudinally from the coronal end and having an inner circumference and an internally threaded section, and
    a plurality of longitudinally extending anti-rotation structures formed at the inner circumference of the interior bore coronal of the internally threaded section, the plurality of longitudinally extending anti-rotation structures comprising a first set of anti-rotation structures constituting a first anti-rotation feature and a second set of anti-rotation structures constituting a second anti-rotation feature which is independent from the first anti-rotation feature,
    wherein the anti-rotation structures of the first set and the anti-rotation structures of the second set extend in part over a common length along the longitudinal axis, and
    wherein the set of anti-rotation structures having a greatest radius, as measured from a central longitudinal axis of the dental implant, start coronally of, or at a same axial location as, the other set of anti-rotation structures, such that both sets of anti-rotation structures can be accessed independently,
    wherein the anti-rotation structures of the first set each have at least one surface extending along a first length and the anti-rotation structures of the second set each have at least one surface extending along a second length, wherein the second length is between ⅓ to ⅔ of the first length, wherein the first set of anti-rotation structures begin closer to the coronal end of the implant than the second set.

2. The dental implant according to claim 1, wherein the first set of anti-rotation structures extend over a greater length of the longitudinal bore than the second set of anti-rotation structures.

3. The dental implant according to claim 1, wherein the second set of anti-rotation structures are totally encompassed by the first set of anti-rotation structures.

4. The dental implant according to claim 1, wherein the common length along the longitudinal axis amounts to at least a half of a length of longer ones of the anti-rotation structures.

5. The dental implant according to claim 1, wherein the anti-rotation structures of the first set are equally profiled transversely to the longitudinal axis and the anti-rotation structures of the second set are equally profiled transversely to the longitudinal axis, wherein the profiles of the first and second sets of anti-rotation structures are not the same.

6. The dental implant according to claim 1, wherein the anti-rotation structures of one of the two sets have a rounded or curved profile and the anti-rotation structures of the other set have an angled profile.

7. The dental implant according to claim 1, wherein the anti-rotation structures of one of the two sets are broader than the anti-rotation structures of the other set.

8. The dental implant according to claim 1, wherein the bore comprises, at the coronal end of the bore, a frustoconical surface tapering inwardly, wherein the common length of the first and second anti-rotation structures is located apical of the frustoconical surface, and wherein the first set of anti-rotation structures begin in said frustoconical surface and the second set begin apically of said frustoconical surface.

9. The dental implant according to claim 1, wherein the anti-rotation structures of each set are located at regularly spaced angular intervals about the longitudinal axis.

10. A dental implant kit comprising:
    a dental implant according to claim 1, and
    an insertion tool for insertion of the dental implant into the bone, the insertion tool comprising a tip which is shaped to engage the first set of anti-rotation structures, such that torque can be transmitted from the tool to the implant via the first anti-rotation feature, the tip being further shaped so as not to engage the second set of anti-rotation structures in a torque transmitting manner.

11. The dental implant kit according to claim 10, further comprising an abutment for connection to the implant, the abutment comprising a connection portion for insertion into the longitudinal bore of the implant, wherein the connection portion comprises an anti-rotation feature shaped to engage the second set of anti-rotation structures without engaging the first set of anti-rotation structures.

12. The dental implant according to claim 1, wherein the first length of the anti-rotation structures of the first set and the second length of the anti-rotation structures of the second set are parallel to the longitudinal axis.

13. The dental implant according to claim 1, wherein at least a portion of the at least one surface of the anti-rotation structures of the first set extends a distance radially further from the central longitudinal axis of the dental implant than at least a portion of the at least one surface the anti-rotation structures of the second set.

14. The dental implant according to claim 13, wherein the entire first length of the anti-rotation structures of the first set extends a distance radially further from the central longitudinal axis of the dental implant than the entire second length of the anti-rotation structures of the second set.

15. The dental implant according to claim 1, wherein the anti-rotation structures of the first set extend onto an exterior surface of both a proximal part and an undercut of the dental implant.

16. A dental implant for insertion in the jaw bone of a patient, comprising:
    an elongated body having a longitudinal axis and a coronal end, an interior blind bore extending longitudinally from the coronal end and having an inner circumference and an internally threaded section, and a plurality of longitudinally extending anti-rotation structures formed at the inner circumference of the interior bore coronal of the internally threaded section, the plurality of longitudinally extending anti-rotation structures comprising a first set of anti-rotation structures constituting a first anti-rotation feature and a second set of anti-rotation structures constituting a second anti-rotation feature which is independent from the first anti-rotation feature, wherein the anti-rotation structures of the first set and the anti-rotation structures of the second set extend in part over a common length along the longitudinal axis, and wherein the set of anti-rotation structures having a greatest radius, as measured from a central longitudinal axis of the dental implant, start coronally of, or at a same axial location as, the other set of anti-rotation structures, such that both sets of anti-rotation structures can be accessed independently, wherein the anti-rotation structures of the first set each have at least one surface extending along a first length and the anti-rotation structures of the second set each have at least one surface extending along a second length, wherein the second length is between ⅓ to ⅔ of the first length, wherein the second set of anti-rotation structures are formed by projections on the interior bore, wherein the common length of the bore is circular cylindrical in shape and has a radius r, the projections extending inwardly of r and being interposed between segments of bore having radius r, wherein the anti-rotation structures of the first set are formed by indentations, and wherein at least some of the indentations of the first set are formed in the projections of the second set.

17. A dental implant for insertion in the jaw bone of a patient, comprising:

an elongated body having a longitudinal axis and a coronal end, an interior blind bore extending longitudinally from the coronal end and having an inner circumference and an internally threaded section, and a plurality of longitudinally extending anti-rotation structures formed at the inner circumference of the interior bore coronal of the internally threaded section, the plurality of longitudinally extending anti-rotation structures comprising a first set of anti-rotation structures constituting a first anti-rotation feature and a second set of anti-rotation structures constituting a second anti-rotation feature which is independent from the first anti-rotation feature, wherein the anti-rotation structures of the first set and the anti-rotation structures of the second set extend in part over a common length along the longitudinal axis, and wherein the set of anti-rotation structures having a greatest radius, as measured from a central longitudinal axis of the dental implant, start coronally of, or at a same axial location as, the other set of anti-rotation structures, such that both sets of anti-rotation structures can be accessed independently, wherein the anti-rotation structures of the first set each have at least one surface extending along a first length and the anti-rotation structures of the second set each have at least one surface extending along a second length, wherein the second length is between ⅓ to ⅔ of the first length, wherein the second set of anti-rotation structures are formed by projections on the interior bore, wherein the common length of the bore is circular cylindrical in shape and has a radius r, the projections extending inwardly of r and being interposed between segments of bore having radius r, wherein the anti-rotation structures of the first set are formed by indentations, wherein the common length of the bore has a radius r, and wherein the first set of anti-rotation structures comprise anti-rotation surfaces located radially beyond r and the second set of anti-rotation structures comprise anti-rotation surfaces located inwards of r.

18. A dental implant for insertion in the jaw bone of a patient, comprising:

an elongated body having a longitudinal axis and a coronal end, an interior blind bore extending longitudinally from the coronal end, and a first set of longitudinally extending anti-rotation structures constituting a first anti-rotation feature and a second set of longitudinally extending anti-rotation structures constituting a second anti-rotation feature, the anti-rotation structures of the first set and the anti-rotation structures of the second set extending at least in part over a common length of the bore, wherein the second set of anti-rotation structures are formed by projections on the interior bore, wherein the common length of the bore is circular cylindrical in shape and has a radius r, the projections extending inwardly of r and being interposed between segments of bore having radius r, wherein the anti-rotation structures of the first set are formed by indentations, wherein the first set of anti-rotation structures extend over a greater length of the longitudinal bore than the second set of anti-rotation structures.

19. The dental implant according to claim 18, wherein the second set of anti-rotation structures are totally encompassed by the first set of anti-rotation structures.

20. The dental implant according to claim 18, wherein the common length along the longitudinal axis amounts to at least a half of a length of longer ones of the anti-rotation structures.

21. The dental implant according to claim 18, wherein the anti-rotation structures of the first set are equally profiled transversely to the longitudinal axis and the anti-rotation structures of the second set are equally profiled transversely to the longitudinal axis, wherein the profiles of the first and second sets of anti-rotation structures are not the same.

22. The dental implant according to claim 18, wherein the anti-rotation structures of one of the two sets have a rounded or curved profile and the anti-rotation structures of the other set have an angled profile.

23. The dental implant according to claim 18, wherein the anti-rotation structures of one of the two sets are broader than the anti-rotation structures of the other set.

24. The dental implant according to claim 18, wherein the bore comprises, at the coronal end of the bore, a frustoconical surface tapering inwardly, wherein the common length of the first and second anti-rotation structures is located apical of the frustoconical surface, and wherein the first set of anti-rotation structures begin in said frustoconical surface and the second set begin apically of said frustoconical surface.

25. The dental implant according to claim 18, wherein the anti-rotation structures of each set are located at regularly spaced angular intervals about the longitudinal axis.

26. The dental implant according to claim 18, wherein at least some of the indentations of the first set are formed in the projections of the second set.

27. The dental implant according to claim 18, wherein the first set of anti-rotation structures comprise anti-rotation surfaces located radially beyond r and the second set of anti-rotation structures comprise anti-rotation surfaces located inwards of r.

28. A dental implant for insertion in the jaw bone of a patient, comprising:
    an elongated body having a longitudinal axis and a coronal end,
    an interior blind bore extending longitudinally from the coronal end, and
    a first set of longitudinally extending anti-rotation structures constituting a first anti-rotation feature and a second set of longitudinally extending anti-rotation structures constituting a second anti-rotation feature, the anti-rotation structures of the first set and the anti-rotation structures of the second set extending at least in part over a common length of the bore, wherein the second set of anti-rotation structures are formed by projections on the interior bore, wherein the common length of the bore is circular cylindrical in shape and has a radius r, the projections extending inwardly of r and being interposed between segments of bore having radius r, wherein the anti-rotation structures of the first set are formed by indentations, wherein the first set of anti-rotation structures begin closer to the coronal end of the implant than the second set.

29. A dental implant for insertion in the jaw bone of a patient, comprising:
    an elongated body having a longitudinal axis and a coronal end, and
    an interior blind bore extending longitudinally from the coronal end, comprising an inwardly tapered frustoconical surface extending from the coronal end, and, apically adjacent to the frustoconical surface a cylindrical portion,
    wherein the bore further comprises a first set of equally profiled longitudinally extending anti-rotation structures constituting a first anti-rotation feature and a second set of equally profiled longitudinally extending anti-rotation structures constituting a second anti-rotation feature, the anti-rotation structures of the first and second set extending at least over a common length along the longitudinal axis apical of the frustoconical surface, and
    wherein the set of anti-rotation structures having a greatest radius start coronally of the other set of anti-rotation structures, such that both sets of anti-rotation structures can be accessed independently,
    wherein the anti-rotation structures of the first set have a first length and the anti-rotation structures of the second set have a second length, wherein the second length is between ⅓ to ⅔ of the first length, wherein the first set of anti-rotation structures begin closer to the coronal end of the implant than the second set.

\* \* \* \* \*